(12) United States Patent  
Lee

(10) Patent No.: US 6,199,425 B1
(45) Date of Patent: Mar. 13, 2001

(54) APPARATUS AND METHOD FOR TESTING THRUST BEARINGS

(75) Inventor: Chen-Hsiung Lee, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/362,259

(22) Filed: Jul. 28, 1999

(51) Int. Cl.⁷ .................................................. G01N 19/02
(52) U.S. Cl. ...................................................... 73/9
(58) Field of Search .............................. 73/865.9, 865.3, 73/9, 10, 862.541

(56) References Cited

U.S. PATENT DOCUMENTS

| 3,023,604 | * | 3/1962 | Gordon et al. | 73/9 |
| 3,685,342 | | 8/1972 | Gordon. | |
| 4,493,514 | | 1/1985 | Henry, IV. | |
| 4,763,508 | | 8/1988 | Buck. | |
| 5,311,763 | | 5/1994 | Gibbs, Jr. et al. | |

FOREIGN PATENT DOCUMENTS

1515088 * 10/1989 (SU) .......................................... 73/9

* cited by examiner

*Primary Examiner*—Robert Raevis
(74) *Attorney, Agent, or Firm*—Robert B. Martin; Felsman, Bradley, Vaden, Gunter & Dillon, LLP

(57) ABSTRACT

A device for testing the take off speed of a thrust bearing in a disk drive spindle motor is disclosed. The device has a stationary torsion transducer that is used to support a drive shaft of the spindle motor. A load motor located adjacent to the transducer rotates the motor about the shaft while applying a radial load to the spindle motor through a belt. The load motor is attached to a linear stage which generates selected radial loads. In one version, the device also uses a ring magnet to attract the housing of spindle motor. The magnetic attraction imposes an axial force on the spindle motor and an equal reactive load on the thrust bearing. The axial load is such that the take off speed for the thrust bearing is much greater than that for the journal bearings. Under these conditions, the friction torque is dominated by the thrust bearing so that an accurate assessment of its quality may be assessed. As an alternative to the magnet, air jets may be used to apply a similar axial load to the thrust bearing.

10 Claims, 4 Drawing Sheets

APPARATUS AND METHOD FOR TESTING THRUST BEARINGS

BACKGROUND OF THE INVENTION

1. Technical Field

This invention relates in general to hydrodynamic bearings and in particular to an apparatus and method for testing a hydrodynamic thrust bearing in a disk drive spindle motor.

2. Background Art

In hydrodynamic lubrication theory, it is well known that the coefficient of friction is velocity dependent. This relationship is known as the Stribeck curve (FIG. 1). For example, when the rotational speed of a fluid hydrodynamic bearing (FDB) is low, the friction torque is high due to solid contact between the elements of the bearing. This is the "boundary lubrication" area indicated in FIG. 1. However, as the rotational speed is increased, a fluid film begins to form which decreases friction. Since the fluid film is not fully developed at this stage, the contact between the components is intermittent. This second stage is known as "mixed lubrication." In the final stage, the bearing has a critical or "take off" speed where the fluid film becomes fully developed and friction is at a minimum. This last stage is known as "full fluid lubrication." Thereafter, friction gradually increases as a linear function of viscous drag.

The take off speed 10 of one type of journal bearing in a disk drive spindle motor is illustrated in FIG. 2. Take off speed is a function of bearing design, surface roughness, sufficient oil, excessive tilt, and external load. If the take off speed for a particular bearing is higher than its design level, a defect of some sort is present in the assembly. Thus, bearings may be tested in this manner in the assembly line to assure their quality prior to assembly into the end product.

In the prior art, an apparatus for testing hydrodynamic rotary or journal bearings has been developed. In this apparatus (FIG. 3), an object such as a disk drive spindle motor 11 containing journal bearings 13 and a thrust bearing 15, has a coaxial drive shaft 17 that is rigidly mounted to a stationary torsion transducer 21 for rotation therewith. A load motor 23 rotates the motor 11 relative to the shaft 17 by applying a transverse or side load to spindle motor 11 through a flexible belt 25. Load motor 23 is mounted to a linear stage 27 which generates selected radial load forces from load motor 23 to spindle motor 11. A load cell 29 monitors the load exerted by linear stage 27. Unfortunately, this method is only capable of testing the take off speed of journal bearings 13, not that of the thrust bearing 15. Thus, a method and apparatus for testing the take off speed of a thrust bearing is needed.

SUMMARY OF THE INVENTION

A device for testing the take off speed of a thrust bearing in a disk drive spindle motor is disclosed. The device has a stationary torsion transducer that is used to support a drive shaft of the spindle motor. A load motor located adjacent to the transducer rotates the motor about the shaft while applying a radial load to the spindle motor through a belt. The load motor is attached to a linear stage which generates selected radial loads. In one version, the device also uses a ring magnet to attract the housing of spindle motor. The magnetic attraction imposes an axial force on the spindle motor and an equal reactive load on the thrust bearing. The axial load is such that the take off speed for the thrust bearing is much greater than that for the journal bearings. Under these conditions, the friction torque is dominated by the thrust bearing so that an accurate assessment of its quality may be assessed. As an alternative to the magnet, air jets may be used to apply a similar axial load to the thrust bearing.

BRIEF DESCRIPTION OF THE DRAWINGS

So that the manner in which the features, advantages and objects of the invention, as well as others which will become apparent, are attained and can be understood in more detail, more particular description of the invention briefly summarized above may be had by reference to the embodiment thereof which is illustrated in the appended drawings, which drawings form a part of this specification. It is to be noted, however, that the drawings illustrate only a preferred embodiment of the invention and is therefore not to be considered limiting of its scope as the invention may admit to other equally effective embodiments.

BEST MODE FOR CARRYING OUT THE INVENTION

Figure 1:
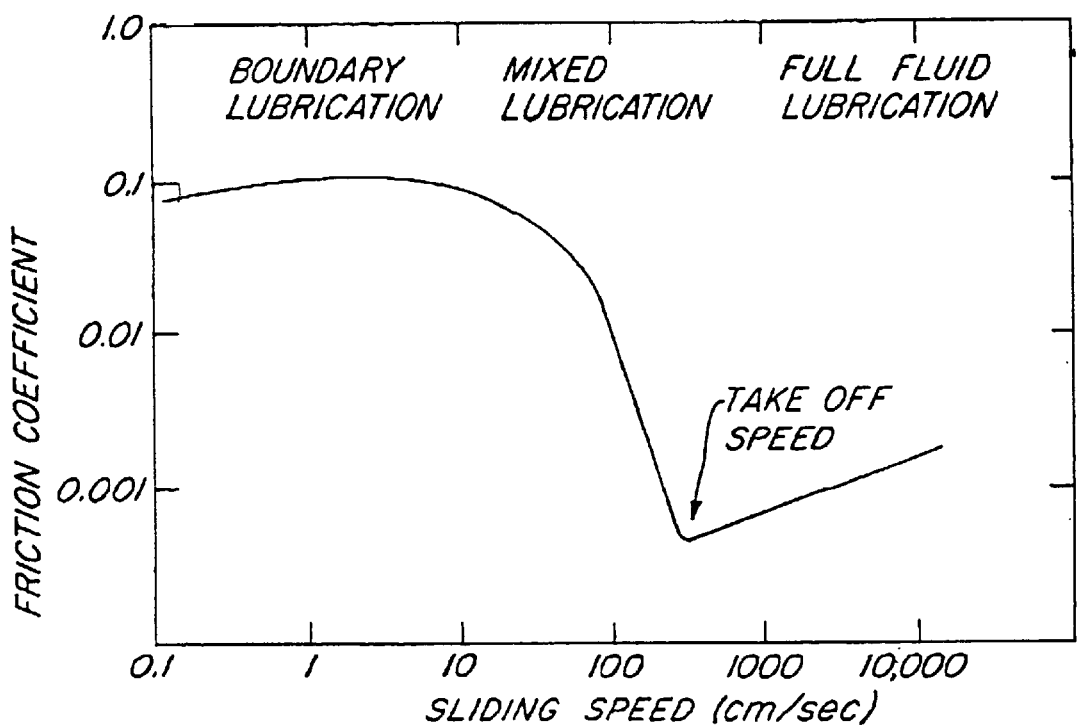
FIG. 1 is a plot of the Stribeck curve depicting the coefficient of friction as a function of sliding speed.
Figure 2:
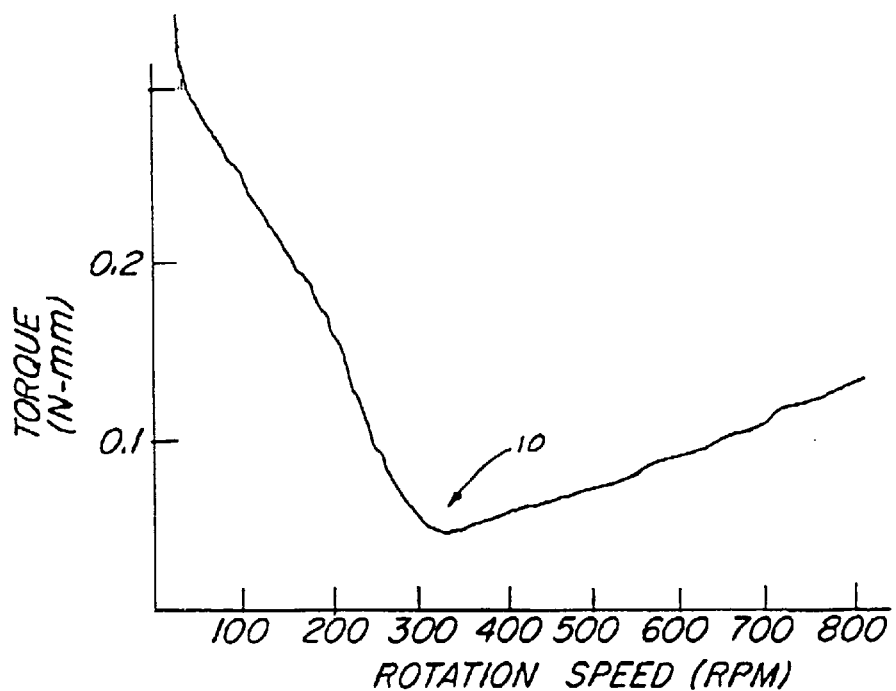
FIG. 2 is a plot of torque in a hydrodynamic bearing as a function of rotational speed.
Figure 3:
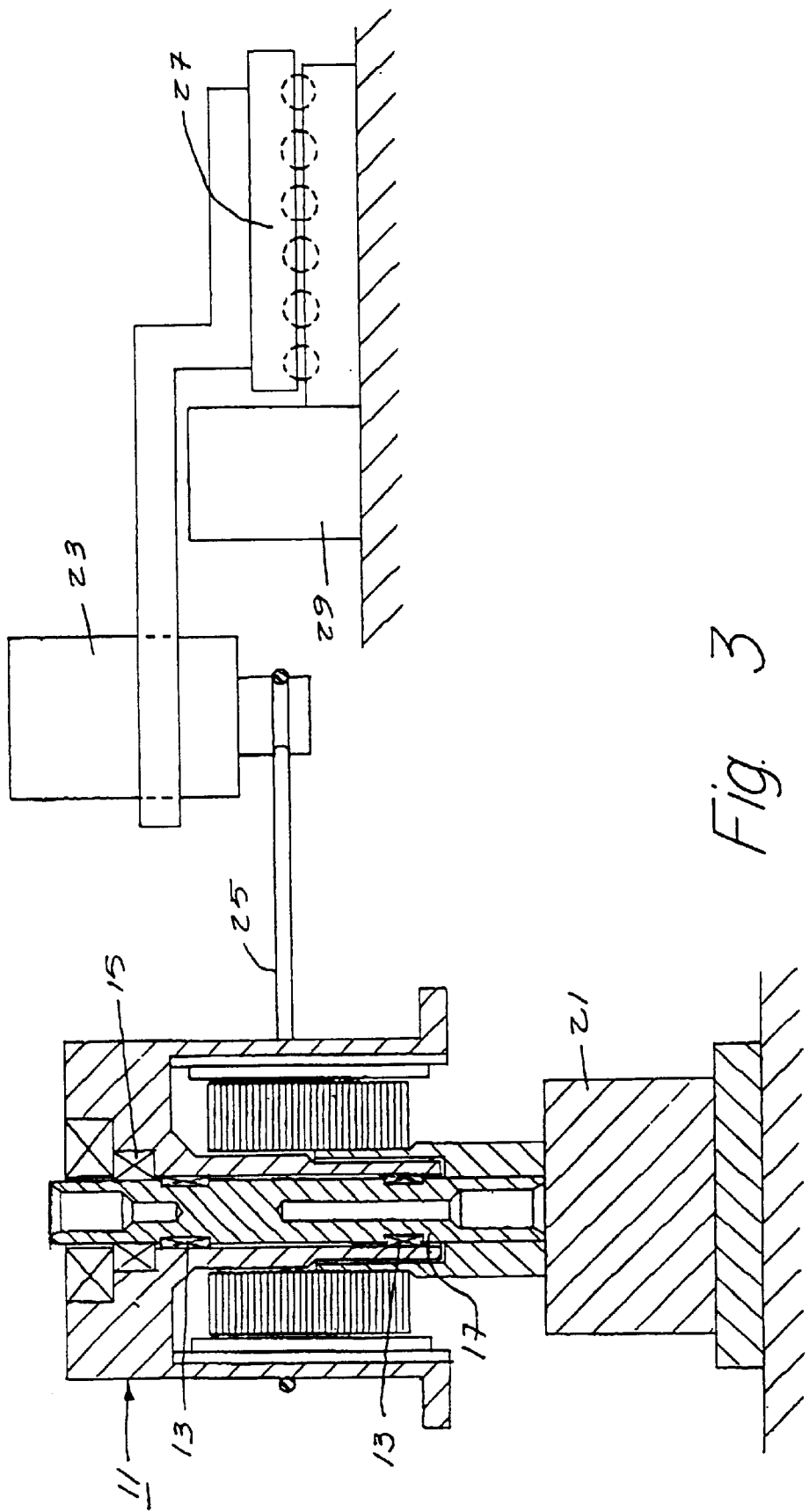
FIG. 3 is a partial sectional side view of a prior art apparatus for testing the journal bearings in a spindle motor.
Figure 4:
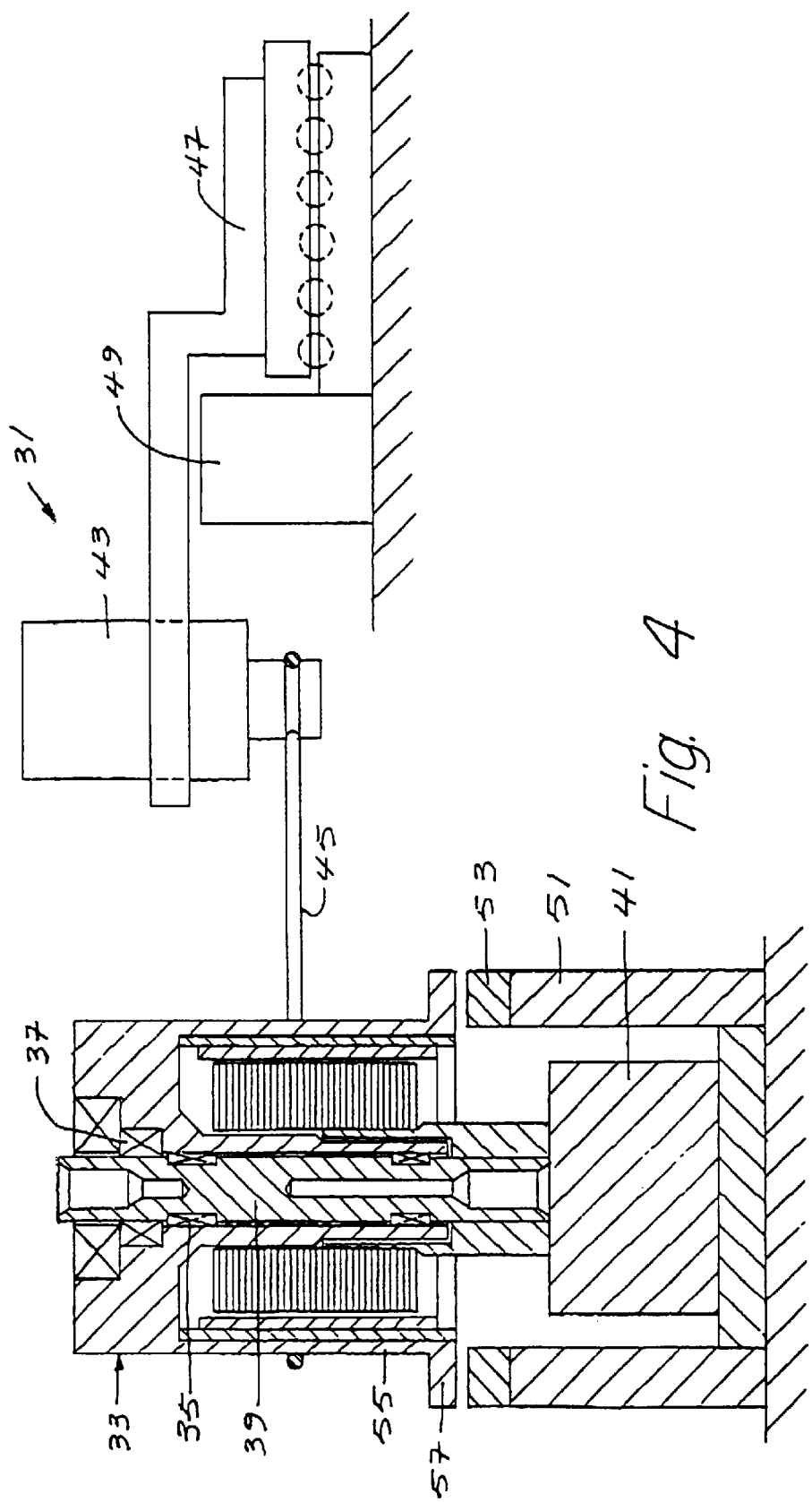
FIG. 4 is a partial sectional side view of a first embodiment of an apparatus for testing the journal bearings in a spindle motor and is constructed in accordance with the invention.

Referring to FIG. 4, a first embodiment of an apparatus 31 for testing the hydrodynamic bearings in a disk drive spindle motor 33 is shown. Spindle motor 33 contains journal bearings 35 and a thrust bearing 37 for supporting a coaxial drive shaft 39. Drive shaft 39 is rigidly mounted to a stationary torsion transducer 41 of apparatus 31. A load motor 43 rotates the spindle motor 33 relative to the shaft 39 by applying a side or radial load to spindle motor 33 through a flexible belt 45. Alternatively, spindle motor 33 could be mounted to transducer 41 and shaft 39 could be rotated by load motor 43. Load motor 43 is mounted to a linear stage 47 which generates selected radial load forces from load motor 43 to spindle motor 33. A load cell 49 monitors the load exerted by linear stage 47.

Apparatus 31 also comprises a ferrous-based, cylindrical hub 51 that surrounds torsion transducer 41. A ring magnet 53 is mounted to an upper end of hub 51 and is axially polarized in a downward direction. When the housing 55 of spindle motor 33 is formed from ferrous materials, an external flange 57 on the lower end of spindle motor 33 is attracted to magnet 53. Thus, magnet 53 imposes a downward force on spindle motor 33 and an equal reactive force on thrust bearing 37.

Figure 5:
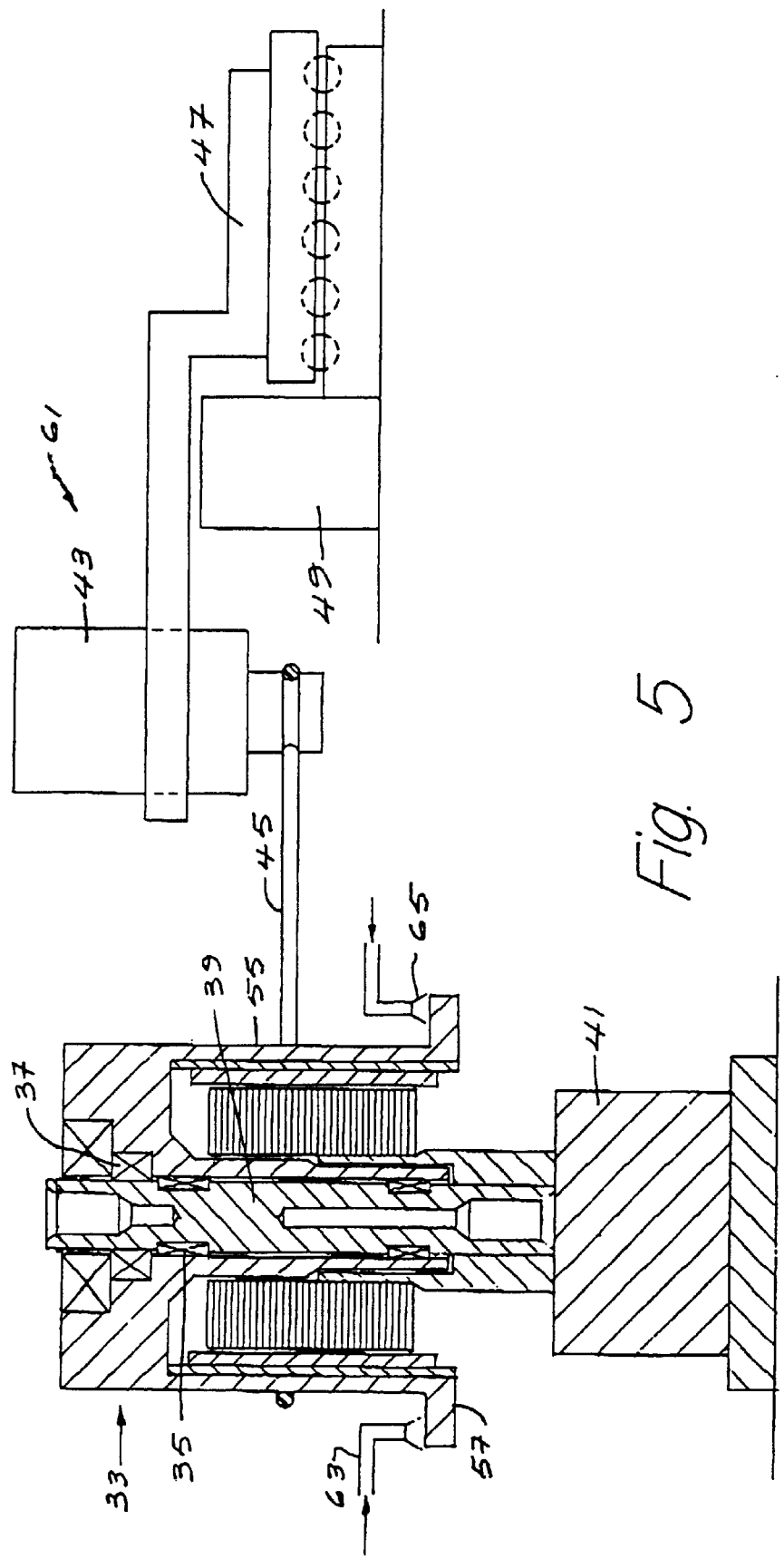
FIG. 5 is a partial sectional side view of a second embodiment of the apparatus of FIG. 4.

In operation, spindle motor 33 is rotated relative to drive shaft 39 by load motor 43. During rotation, the axial load imposed by magnet 53 on flange 57 of spindle motor 33 is approximately two to three times its normal, operational axial load of about 100 grams. This axial load is chosen such that the take off speed for the thrust bearing 37 is about 500 rpm. However, the radial load exerted on the journal bearings 35 by linear stage 47 is chosen such that the take off speed of journal bearings 35 is approximately 50 rpm. Under these conditions, the friction torque of spindle motor 33 is dominated by thrust bearing 37 and an accurate assessment of the quality of thrust bearing 37 may be assessed. With magnet 53 removed from apparatus 31 or a non-ferrous flange 57 on spindle motor 33, apparatus 31 is also capable of testing the journal bearings 35 as described above in the background section of this application. Referring now to FIG. 5, a second embodiment of the invention is shown as apparatus 61. Like apparatus 31, apparatus 61 tests the hydrodynamic bearings in spindle motor 33, described above. Apparatus 61 is identical to apparatus 31 except that hub 51 and magnet 53 have been replaced by a plurality of air jets 63. Air jets 63 are located above flange 57 of spindle motor 33 and direct streams of air 65 downward against the upper surface of flange 57. Air jets 63 may also comprise a single, annular air manifold or other suitable means for directing air against spindle motor 33. This second embodiment is suitable for use with either ferrous or non-ferrous flanges 57. Air jets 63 impose a downward force on spindle motor 33 and an equal reactive force on thrust bearing 37. In operation, apparatus 61 works in the same manner as apparatus 31 in order to test the quality of thrust bearings during manufacturing.

The invention has several advantages. The testing device may be used to manipulate the take off speeds of the thrust and journal bearings of manufactured goods, such as a spindle motor disk drive, in order to test the quality of the bearings. When the take off speed performance of a selected one of the goods exceeds the known or predicted value, the bearing assembly must have some form of defect. An axial load is imposed on the thrust bearing without physical contact with the spindle motor. This load may be applied through a magnet, air jets, or equivalent means.

While the invention has been shown or described in only some of its forms, it should be apparent to those skilled in the art that it is not so limited, but is susceptible to various changes without departing from the scope of the invention.

I claim:

1. An apparatus for testing the take off speed of a thrust bearing in a device having a housing, a rotary shaft, and a journal bearing for radially supporting the shaft within the housing, wherein the thrust bearing axially supports the shaft within the housing, the apparatus comprising:

a torsion transducer for mounting the device thereto and measuring the torque thereof;

a load motor located adjacent to the torsion transducer for rotating the device and applying radial loads to the device;

a linear stage mounted to the load motor for selectively generating radial load forces on the device;

a load cell mounted adjacent to the linear stage for monitoring the radial load exerted by the linear stage on the device;

an axial load applicator that selectively applies an axial load on the device and an equal reactive force on the thrust bearing such that the friction torque generated by the device is dominated by the thrust bearing in order to measure the take off speed of the thrust bearing; and wherein the axial load applicator comprises a magnet.

2. The apparatus of claim 1 wherein the axial load applicator is adapted to provide the axial load without any physical contact with the device.

3. The apparatus of claim 1 wherein the radial and axial loads applied to the device are selected such that the take off speed for the thrust bearing is approximately ten times greater than that of the journal bearing.

4. The apparatus of claim 1 wherein the drive shaft of the device is stationarily mounted to the torsion transducer, the load motor rotates the housing and applies the radial load to the housing, and wherein the axial load applicator applies the axial load to the housing.

5. The apparatus of claim 1 wherein the housing has a flange of ferrous metal, and the magnet is mounted to the torsion transducer for attracting the flange.

6. An apparatus for testing the take off speed of a thrust bearing in a device having a housing, a rotary shaft, and a journal bearing for radially supporting the shaft within the housing, wherein the thrust bearing axially supports the shaft within the housing, the apparatus comprising:

a stationary torsion transducer for mounting the shaft of device thereto and measuring the torque thereof;

a load motor located adjacent to the torsion transducer for rotating the housing of the device relative to the shaft and applying radial loads to the housing;

a linear stage mounted to the load motor for selectively generating radial load forces on the housing;

a load cell mounted adjacent to the linear stage for monitoring the radial load exerted by the linear stage on the housing;

an axial load applicator that selectively applies an axial load on the housing and an equal reactive force on the thrust bearing such that the friction torque generated by the device is dominated by the thrust bearing in order to measure the take off speed of the thrust bearing; wherein the axial load applicator is adapted to provide the axial load without any physical contact with the device; and wherein the axial load applicator comprises a magnet.

7. The apparatus of claim 6 wherein the radial and axial loads applied to the device are selected such that the take off speed for the thrust bearing is approximately ten times greater than that of the journal bearing.

8. The apparatus of claim 6 wherein the housing has a flange of ferrous metal, and the magnet is mounted to the torsion transducer for attracting the flange.

9. A method for testing the take off speed of a thrust bearing, the method comprising:

(a) providing a device having a housing, a rotary shaft, a thrust bearing for axially supporting the shaft within the housing, and a journal bearing for radially supporting the shaft within the housing;

(b) mounting one of the housing and the shaft to a torsion transducer for measuring the friction torque generated by the device;

(c) rotating the other of the housing and the shaft and applying a radial load thereto;

(d) applying a selected axial load to the device such that an equal reactive force is exerted on the thrust bearing and the friction torque generated by the device is dominated by the thrust bearing;

(e) measuring the friction torque with the torsion transducer such that the take-off speed of the thrust bearing may be ascertained while the loads are being applied; and wherein step (d) comprises attracting an axial end of the device with a magnetic force.

10. The method of claim 9 wherein step (b) comprises mounting the drive shaft of the device to the torsion transducer, wherein step (c) comprises rotating the housing and applying the radial load to the housing, and wherein step (d) comprises applying the axial load to the housing.

* * * * *